(12) United States Patent
Oh et al.

(10) Patent No.: US 6,673,840 B1
(45) Date of Patent: Jan. 6, 2004

(54) USE OF LIPOXYGENASE METABOLITE OF ARACHIDONIC ACID AND ITS DERIVATIVES IN CAPSAICIN-CHANNEL AGONIST

(75) Inventors: Uhtaek Oh, Eul-gi Apt., 615-102, Sanbon 2-dong, Kunpo-si, 435-042, Kyunggi-do (KR); Sun Wook Hwang, Seoul (KR)

(73) Assignee: Uhtaek Oh, Kyunggi-do (KR)

( * ) Notice: Subject to any disclaimer, the term of this patent is extended or adjusted under 35 U.S.C. 154(b) by 0 days.

(21) Appl. No.: 09/762,449

(22) PCT Filed: Aug. 2, 1999

(86) PCT No.: PCT/KR99/00421

§ 371 (c)(1), (2), (4) Date: Feb. 6, 2001

(87) PCT Pub. No.: WO00/07589

PCT Pub. Date: Feb. 17, 2000

(30) Foreign Application Priority Data

Aug. 7, 1998 (KR) .............................. 98-32208

(51) Int. Cl.[7] .............................................. A61K 31/20
(52) U.S. Cl. ........................................................ 514/558
(58) Field of Search ......................................... 514/558

(56) References Cited

U.S. PATENT DOCUMENTS 5,650,435 A * 7/1997 Madara et al.
5,909,734 A * 6/1999 Peters-Golden et al.

OTHER PUBLICATIONS

Riccio et al. "The effect of 15–HPETE on airways responsiveness and pulmonary cell recruitment in rabbits." British Journal of pharmacology, 122(2), 1997: 249–256.*

Feissmuth and Gilman "G proteins and the regulation of second messenger systems" in Harrison's Principles of Internal Medicine, 13th., 1994:p. 426–431.*

Edenius et al., Biochimica et Biophysica Acta, 1994; 1210 (3): 361–367.*

Aharony et al., Biochimica et Biophysica Acta, 1982; 718(20: 193–200.*

An article entitled, "The Cloned Capsaicin Receptor Integrates Multiple Pain–Producing Stimuli", By Tominaga et al., published Sep. 1998, vol. 21, pp. 531–543.

An article entitled, "The capsaicin receptor: a heat–activated ion channel in the pain pathway", By Caterina et al., published Oct. 1997, vol. 389, pp. 816–824.

An article entitled, "Direct activation of capsaicin receptors by products . . . ", By Hwang et al., published May 23, 2000, vol. 97, No. 11, pp. 6155–6160.

An article entitled, "Capsaicin Binds to Intracellular Domain of the Capsaicin–Activated Ion Channel", By Jung et al., published Jan. 15, 1999, vol. 19, No. 2, pp. 529–538.

An article entitled, "Capsaicin Activates a Nonselective Cation Channel in Cultured Neonatal Rat Dorsal Root Ganlgion Neurons", By Oh et al., published Mar. 1, 1996, vol. 16, No. 5, pp. 1659–1667.

An article entitled, "Vanilloid receptors on sensory nerves mediate the vasodilator action of anandamide", By Zygmunt et al., published Jul. 29, 1999, vol. 400, pp. 452–456.

* cited by examiner

Primary Examiner—Sreeni Padmanabhan
Assistant Examiner—San-ming Hui
(74) Attorney, Agent, or Firm—Bachman & LaPointe, P.C.

(57) ABSTRACT

Disclosed is the use of metabolites produced from arachiconic acid by the catalytic action of lipoxygenase as capsaicin-channel or- receptor agonists. The lipoxygenase metavolites of arachidonic acid and their derivatives can activate the capsaicin channel to excite pain nerves, causing serious pain. In contrast, the capsaicin channel activation of the pain nerves, so that an analgesic effects are brought about. The lipoxygenase metabolites of arachidonic acid can be used as an analgesic and in searching for and developing analgesics.

1 Claim, 15 Drawing Sheets nerve terminal of a pain sensory neuron capsaicin activated channel

USE OF LIPOXYGENASE METABOLITE OF ARACHIDONIC ACID AND ITS DERIVATIVES IN CAPSAICIN-CHANNEL AGONIST

This is a 371 of PCT/KR99/00421, filed Aug. 2, 1999.

BACKGROUND OF THE INVENTION

1. Field of the Invention

The present invention relates to the use of the lipoxygenase metabolites of arachidonic acid and their derivatives as capsaicin-channel or -receptor agonists. More particularly, the present invention relates to the metabolites produced from arachidonic acid by the catalytic action of lipoxygenase, which can be used as an analgesic which is superior in pain-relieving efficacy and free of durg resistance and addition.

2. Description of the Prior Art

Analgesics developed thus far are largely classified into two categories: narcotic and antiphlogistic. The former, exerting its pharmacological effects on the central nervous system, shows potent pain-alleviating activity with accompaniments of strong side effects including resistance and addiction. With an unclear explanation regarding their pharmaceutical mechanism, antiphlogistic analgesics are weaker in pain relief than narcotic analgesics as well as may cause gastric and liver troubles (Insel, 1996; Reisine and Pasternak, 1996).

Referring to FIG. 1, there is illustrated a pain transmission mechanism. When pain from a peripheral organ stimulates a sensory nerve cell, the cell generates a nerve impulse which is then transmitted to the spinal cord in which the nerve impulse is propagated along neurons to many nuclei in the brain. Ultimately, the nerve impulse is transmitted into the pain sensory center of the brain, making the body feel pain (Wills and Coggeshal, 1991; Yaksh, 1986).

Peppers, in both the Orient and the Occident, are used as a spice to provide foods with a hot taste. It is capsaicin (;CAP) that provides the hot taste of pepper. Particularly, CAP is known to be closely related to pain. In the early stages of stimulation, CAP exists sensory nerves, causing serious pain. However, if accumulation of CAP prolongs, there occurs desensitization, leading to an analgesic effect which lasts for a long period of time (Holzer P, Pharmacol Rev. 43:143–201, 1991). In addition, CAP may reportedly serve as a kind of neurotoxin, which allows sensory neurons a conformational change, leading sensory neurons to being permanently damaged (Holzer P, supra; Szallasi and Blumberg, Adv. Pharmacol. 24:123–155, 1993). Recently, active research has been directed to the development of CAP derivatives to potent analgesics, making use of the pain-relieving effect due to the desensitization of CAP (Szallasi and Blumberg, 1996; Rouhi, 1998). Because the neurotoxic effect of CAP is confined only to small sensory neurons, advantage is believed to be taken of CAP to develop addiction-free analgesics which exert their pharmacological actions on the peripheral neuron system, but not on the central nerve system.

The present inventors found a non-selective cation channel which opens when being directly associated with CAP, so as to mediate the neural excitation induced by CAP. This mechanism is schematically depicted in FIG. 2. Up to recent years, it has been known that a whole-cell current is caused by CAP, but single-channel currents which can conduct the whole-cell current response have clearly been revealed. The present inventors found a non-selective cation channel which can be activated by CAP depending on the concentration of CAP and reported that this channel is activated specifically by CAP and inhibited by capsazepine (;CZP), a CAP-receptor antagonist (Oh, et al., 1996).

Also, it was reported that the CAP channel is non-selectively permeable to cations, such as $Na^+$, $Ca^{2+}$, etc., to depolarize the sensory nerve cells (Oh, et al., supra). When CAP is added to the extracellular side of the cell membrane of sensory nerve cells, the CAP channel is activated without the aid of a second messenger, which indicates that the CAP channel is a ligand-gated ion channel (Oh, et al., supra).

The fact that CAP channels, which can be activated by CAP, an exogenous material, exist in sensory nerve cells suggests that there be any endogenous material that can activate the CAP channels. In addition, the research result that shows the reduction of inflammatory pain by CZP, a CAP-receptor antagonist (Kwak, et al., 1998), enables the present inventors to expect that, upon inflammation, endogenous CAP-like substances occur and bind to the CAP channels to activate them, thereby causing pain. Further, because CAP binds to the intracellular side of the CAP channel (Oh, et al., 1996b), the endogenous CAP-like substances are expected to be synthesized within cells.

CAP channels, which play an essential role in causing pain, exist, in abundance, in sensory neurons. When they are, for instance, activated by CAP, the opening of CAP channels causes a strong pain and then the desensitization of the channel shows an analgesic effect. Hence, the endogenous active substances which exert an action on the CAP channels are absolutely possible to use as novel analgesics which can overcome the problems that conventional analgesics have, such as the tolerance and addition of narcotic analgesics and the weak efficacy of antiphlogistic analgesics. Moreover, the substances, if existing, are expectedly almost free of side effects because they are originated from cells. Therefore, if an endogenous active substance, such as a ligand, for CAP channels had been revealed, the substance itself would have been an excellent analgesic as well as served as a model for the development of its analogue compounds which can be used as analgesics with a new concept.

Many researchers have made efforts to find endogenous ligands for CAP channels, but did not succeed in the research in this microscopic world.

The inventor found that metabolic products of lipoxygenase(;LO) activate the CAP channel. The inventor also found that among products of LO, 12-hydroxyeicosatetraenoic acid (12-HPETE) is the most potent and that the two materials are structurally similar.

SUMMARY OF THE INVENTION

Knowledge of the pain generation mechanism in sensory nerves allows the development of analgesics which can relieve pain, leading to the present invention.

It is therefore an object of the present invention to overcome the above problems encountered in prior arts and to provide an analgesic which has superior pain-relieving efficacy and lacks drug resistance and addiction properties.

Based on the present invention, the above object could be accomplished by a provision of the use lipoxygenase metabolites of arachidonic acid as a capsaicin-channel or-receptor agonists.

BRIEF DESCRIPTION OF THE DRAWINGS

The above and other objects and aspects of the invention will become apparent from the following description of embodiments with reference to the accompanying drawings in which.

DETAILED DESCRIPTION OF THE INVENTION

Figure 1A:
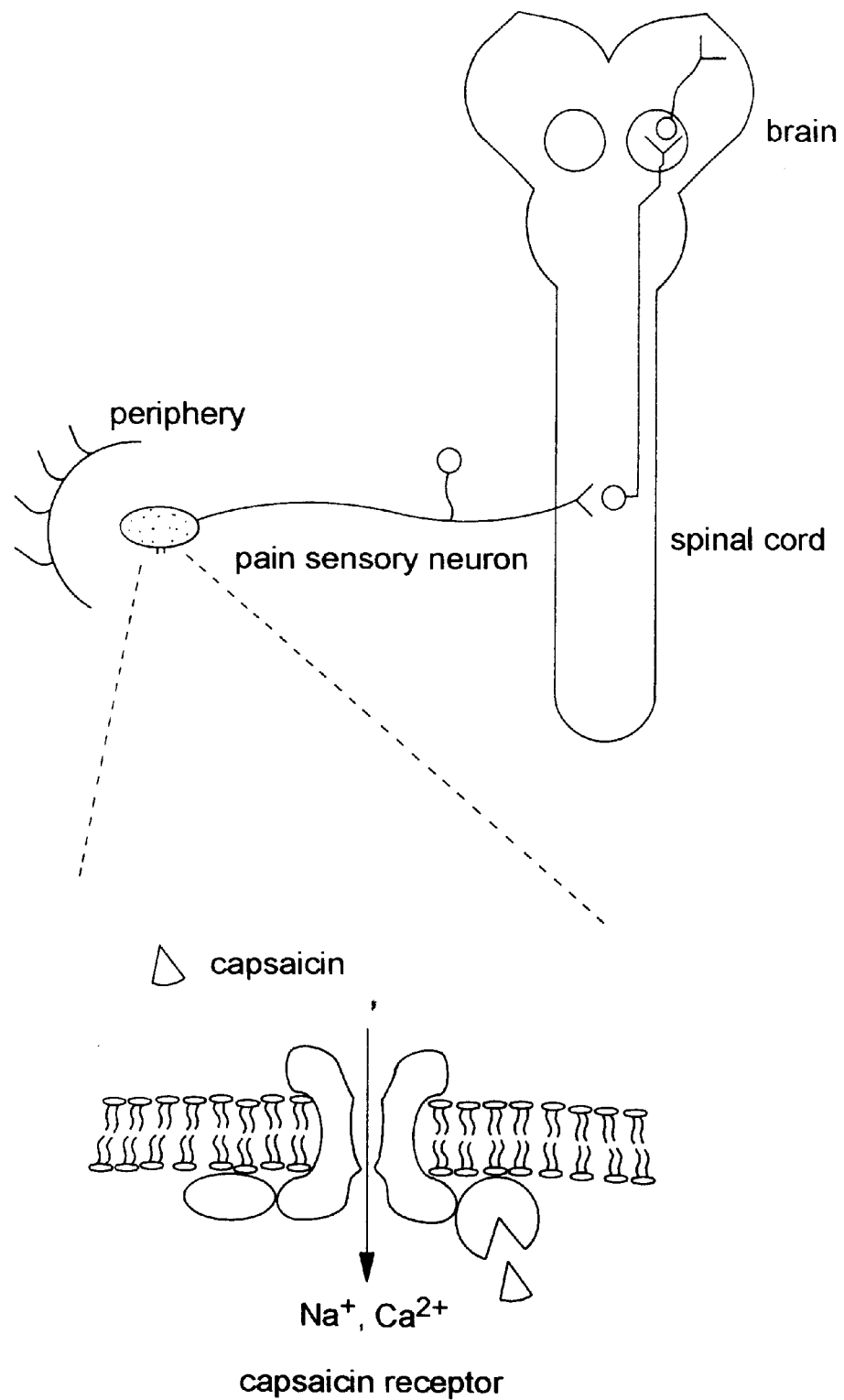
FIG. 1a is a schematic view illustrating a pain transmission pathway.
Figure 1B:
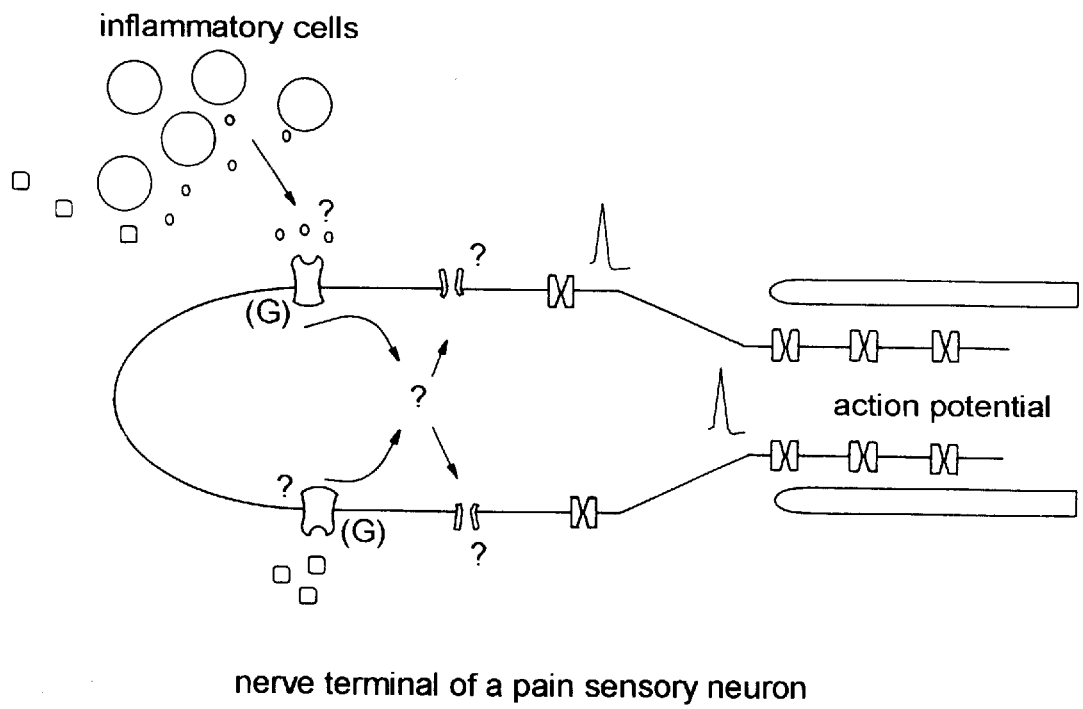
FIG. 1b is a schematic view illustrating a molecular mechanism for the pain signal generation in a sensory neuron.
Figure 2:
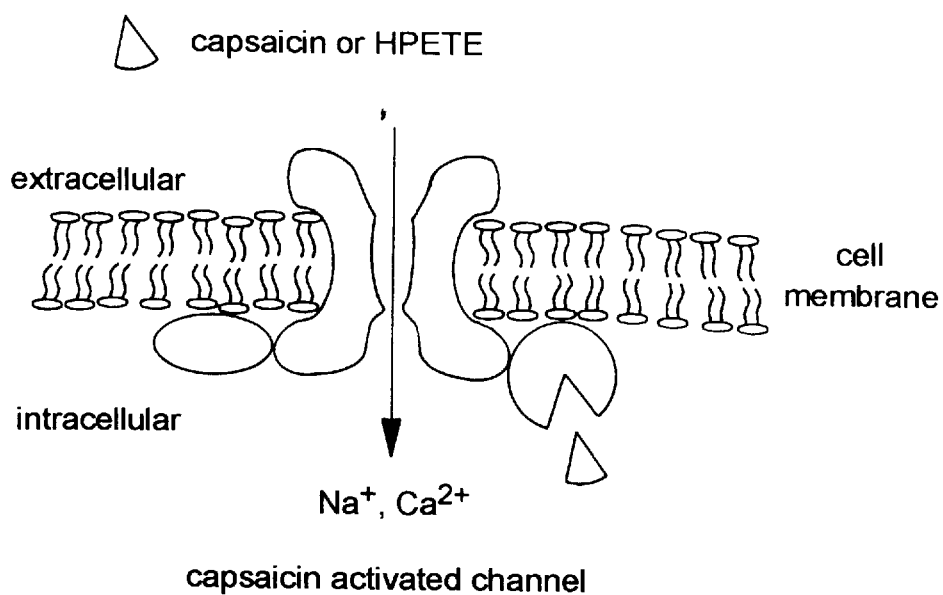
FIG. 2 is a schematic view illustrating a capsaicin channel.

The important metabolites of arachidonic acid result from the catalytic actions of lipoxygenase and cyclooxygenase. The metabolism of arachidonic acid through the enzyme lipoxygenase follows the following schematic reaction pathways 1 to 4.

REACTION PATHWAY 1

5-Lipoxygenase Pathway

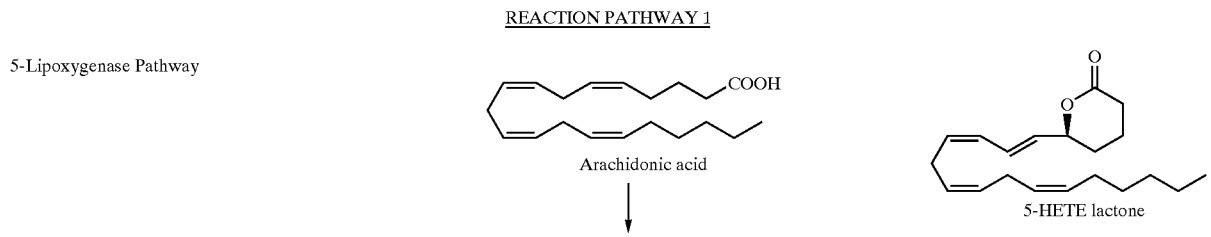

Arachidonic acid

5-HETE lactone

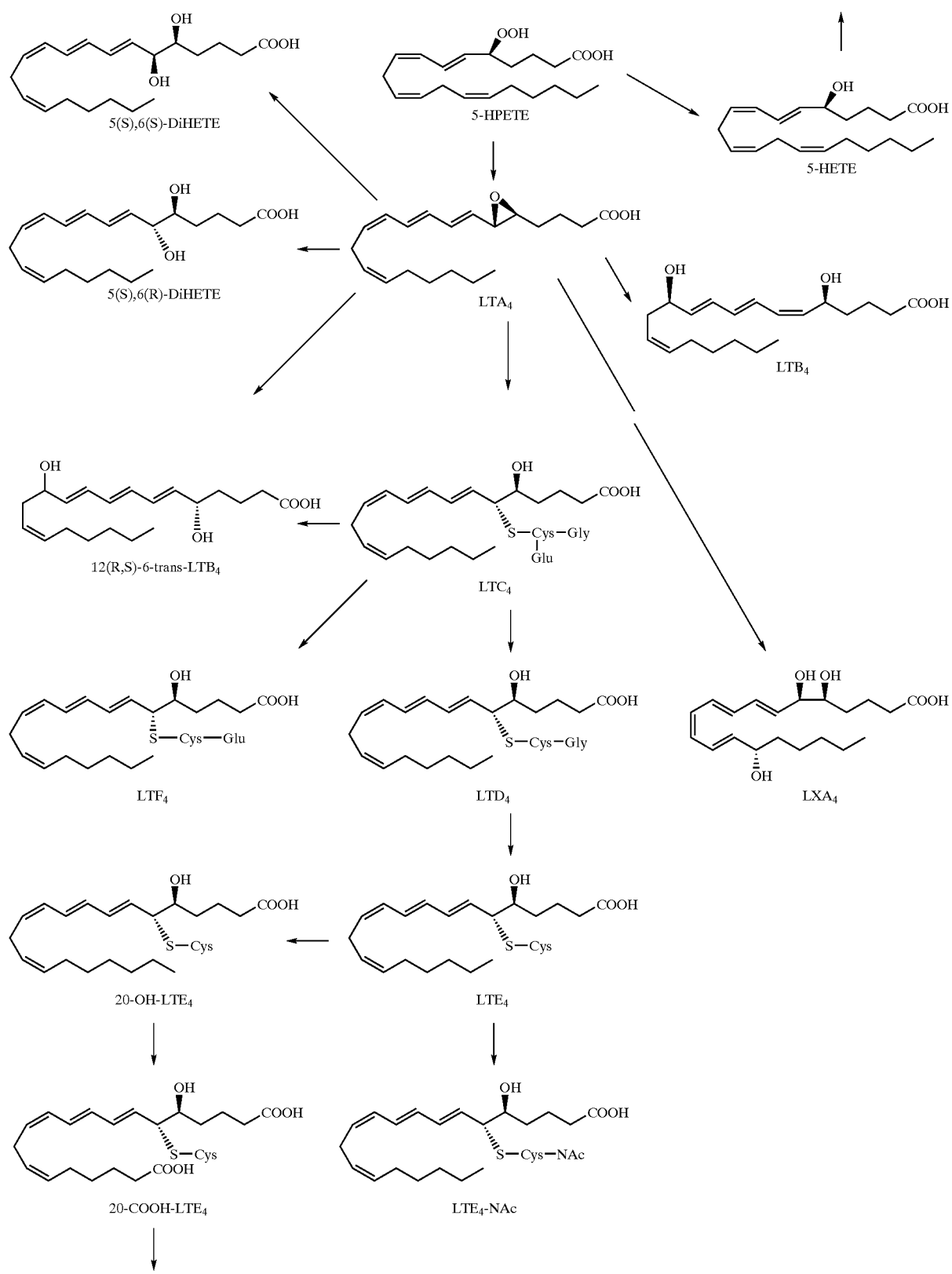

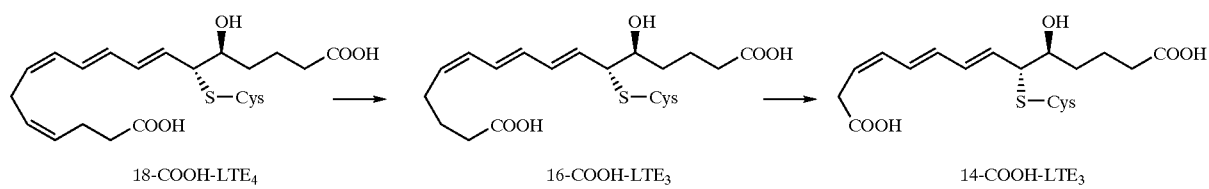
REACTION PATHWAY 2
Metabolism of Leukotriene B₄
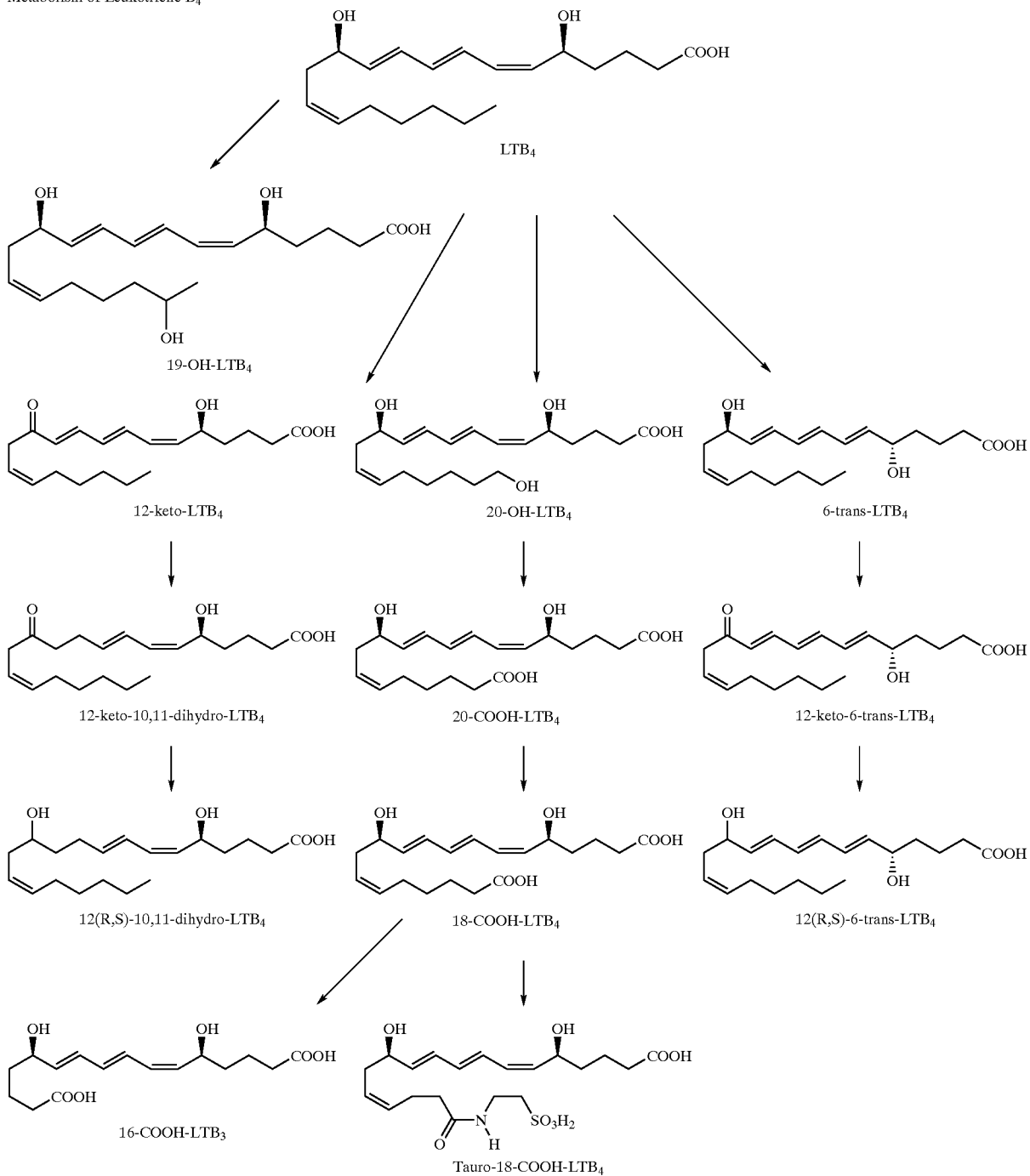

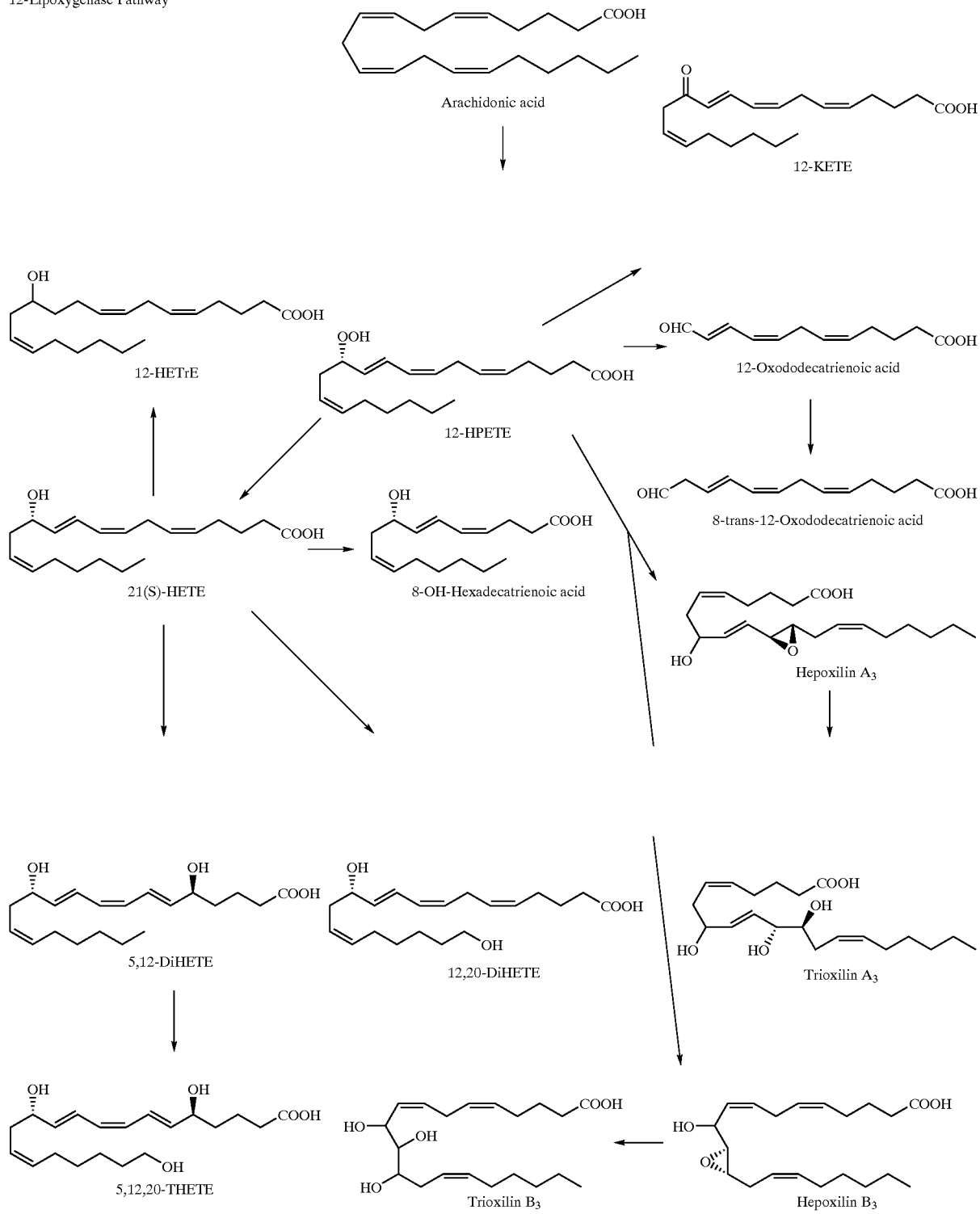

REACTION PATHWAY 4
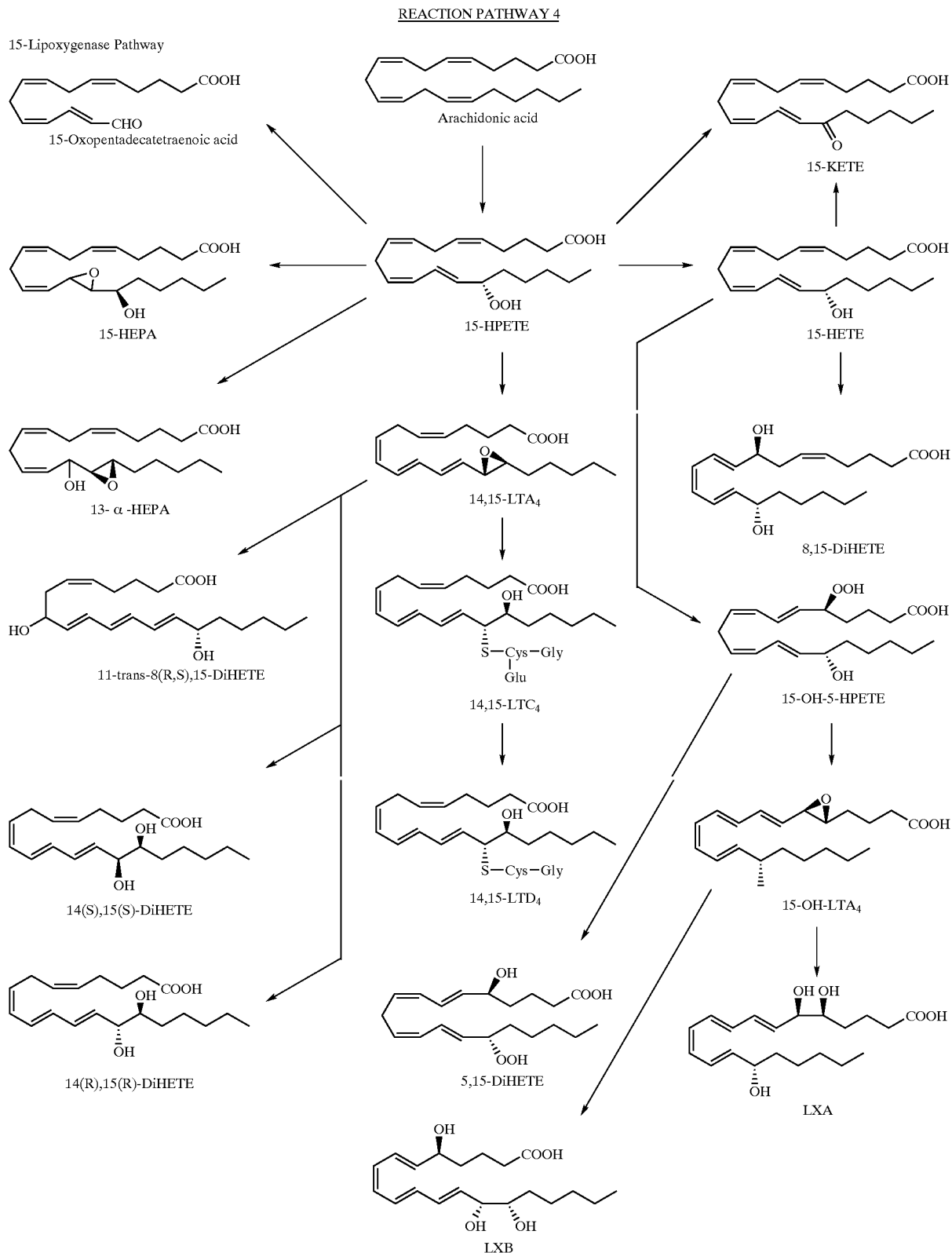
The lipoxygenase metabolites are synthesized in the cytoplasm of various kinds of cells and serve as second messengers to elicit various physiological reactions (Campbell and Halushka, 1995). Of the lipoxygenase metabolites, leukotriene $B_4$ has a potent chemotactic effect, serving as an important factor to cause inflammation (Campbell and Halushka, supra). Lipoxygenase metabolites also perform various functions within cells (Schweitzer et al., 1990; Vaughan et al., 1997). Particularly, they were reported to open ion channels directly. For instance, the lipoxygenase metabolites directly open $K^+$-channels in sensory cells of Aplysia (Butner et al., 1989; Piomelli et al., 1987) and mammalian atrial cells (kim et al., 1986; kurachi et al., 1986).

The reports of the facts that leukotriene $B_4$ or other lipoxygenase metabolites are generated upon inflammation (Samuelsson, 1980) and their subcutaneous injection causes pain (Levine et al., 1984; 1986), strongly suggest that the lipoxygenase metabolites are involved in the pain-inducing mechanism upon inflammation.

In the present invention, use was made of a single channel recording method with the aid of a patch clamp technique (Hamill et al., Pfl gers Arch 391:85–100, 1981) in order to know whether lipoxygenase metabolites activate CAP channels or receptors or not. As a result, it was revealed that, when being added to a cell patch, 12-hydroperoxyeicosatetraenoic acid (hereinafter referred to as '12-HPETE'), one of the lipoxygenase metabolites, activates the CAP channel greatly which is opened by CAP. It was also elicited from the single channel recording experiment that, where the CAP channel is treated with CZP, known as a CAP-channel antagonist, the channel currents generated by 12-HPETE are also blocked. This result means that 12-HPETE directly opens the CAP channel. Furthermore, the ion channel which is opened by the lipoxygenase metabolite shows non-specific selectivity for cations, like the CAP channel. Because the tests are performed in isolated membrane patches without the mediation of intracellular second messengers, lipoxygenase metabolites are believed to exert a direct action on the CAP channel.

Therefore, the present invention provides the use of 12-HPETE as an agonist for CAP channels.

Also, the present invention provides the use of other various lipoxygenase metabolites as agonists for CAP channels.

An examination was made on the efficiency with which the various lipoxygenase metabolites activate CAP channels. To this end, a patch clamp technique was used to record the single channel current generated in the CAP channel to which various lipoxygenase metabolites were applied to measure the open probability (Po) of the CAP channel. To compare the relative potency of each metabolite, the effects of the lipoxygenase metabolites on CAP channels were measured with a reference to 0.5 $\mu M$ CAP. As a consequence, 12-HPETE was found to be the most potent endogenous agonist in activating CAP channels among the ten metabolites. Many of the lipoxygenase showed a function of opening the CAP channels.

The present invention is also characterized in that the endogenous ligand for CAP channels is revealed to be 12-HPETE by investigating the structural similarity between the 12-HPETE and CAP.

When superimposing the structure of 12-HPETE on that of CAP, they both are found to have a curved form like a sickle, showing conformational similarity in total. Besides 12-HPETE, other lipoxygenase metabolites which have a conformational similarity in some degree to CAP also activate CAP channels. In other words, the lipoxygenase metabolites which are low in CAP-channel agonistic potency also show poor conformational similarity to CAP. This phenomenon can be utilized to search for endogenous ligands which are specific for CAP-channels.

A better understanding of the present invention may be obtained in light of the following examples which are set forth to illustrate, but are not to be construed to limit the present invention.

EXAMPLE I

Activity of Lipoxygenase Metabolites in Activation of CAP Channel

A single channel current recording method using a patch clamp technique (Hamill et al., supra; Oh et al., 1996a) was used to know whether the lipoxygenase metabolites directly activate the CAP channel.

Because the binding site of CAP was located on the intracellular side of the channel (Oh et al., 1996b), the metabolites were applied to the intracellular sides of cell membrane patches.

Figure 4:
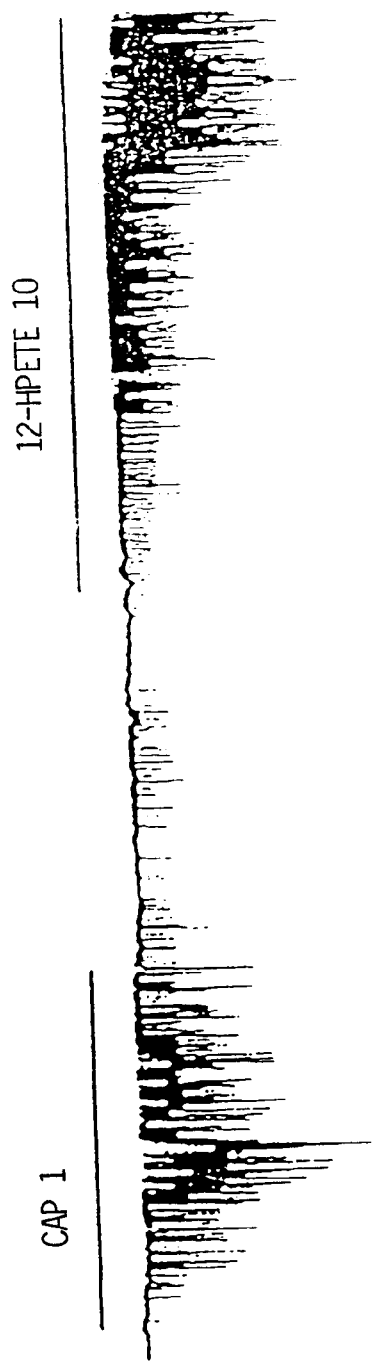
FIG. 4 shows channel currents in a sensory neuron activated by 10 $\mu$M of 12-HPETE and 0.5 $\mu$M of CAP as measured by a single channel recording with the aid of a patch clamp technique.
Figure 5:
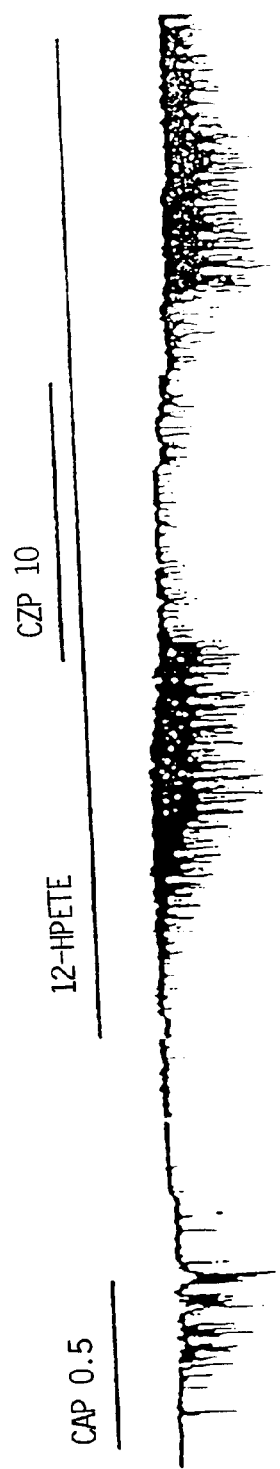
FIG. 5 shows that single channel currents activated by 12-HPETE are inhibited by 10 $\mu$M of capsazepine (czp), indicating that the 12-HPETE-mediated channel can be opened by CAP.

With reference to FIG. 4, there is shown a single channel current which was greatly generated when 0.5 $\mu M$ of CAP was added to an experimental bath containing an inside-out membrane patch. A similar single channel current was observed when 2 $\mu M$ of 12-HPETE were added to the same patch, as shown in FIG. 4. The activation of CAP channels by 12-HPETE (2–20 $\mu M$) was detected from 88 patches of the 97 patch samples tested. Such single channel currents were not observed when 10 $\mu M$ of CZP, known as a CAP-channel antagonist, were present, as demonstrated in FIG. 5. 12-HPETE increased the Po channel open probability from 0.0 to 0.019±0.0002 (n=4) while the Po was greatly decreased to 0.001±0.00002 in the co-existence of 10 $\mu M$ of CZP and 10 $\mu M$ of 12-HPETE.

For comparison between the amplitude of the channel currents generated when the CAP channels were opened by 12-HPETE and CAP, respectively, an analysis was taken on the aptitude of the channel currents. As a result, no differences were found between the amplitudes of the single channel currents generated at a membrane at a membrane potential of 60 mV by CAP (2.72±0.06 pA, n=9) and by 12-HPETE (2.68±0.012 pA, n=8).

Figure 6:
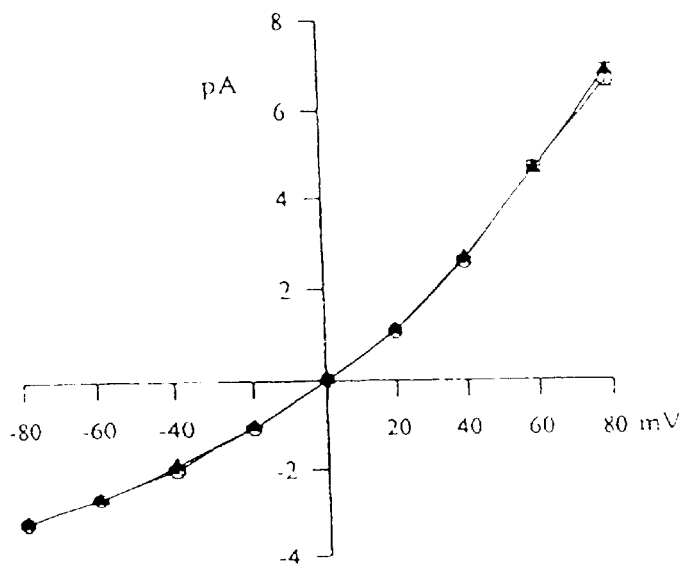
FIG. 6 is a current-voltage curve obtained by measuring the magnitude of the single channel currents at various membrane potentials after administering 12-HPETE in an inside-out patch while the membrane potential was increased by a 20 mV interval from −80 mV up to +80 mV. In the figure, the symbol ▲ stands for 12-HPETE and the symbol ○ for CAP.

Current-voltage characteristic curves of the channel currents generated by CAP and 12-HPETE were obtained and compared. The Current-voltage characteristic curve of the channel currents activated by CAP was completely overlapped with that of the currents activated by 12-HPETE, as seen in FIG. 6, which indicates that the channel which 12-HPETE opens the same channel which CAP does so. In addition, the identification of the channels which were respectively activated by the two agonists was further confirmed by the fact that all the single channel currents generated by 12-HPETE and other lipoxygenase metabolites exhibit the same tendency to outward rectification as shown in the current-voltage characteristic curve obtained by administering CAP (Oh, et al., supra).

An examination was made of the ion selectivity of the channel activated by 12-HPETE in light of the permeability of the channel for various cations. In this regard, after a 140 mM $Na^+$ solution in the bath containing 2~10 $\mu M$ 12-HPETE was charged to 140 mM $K^+$ solution, a measurement was made on the magnitude of the single channel currents at various membrane potentials ranging from −80 mV to +80 mV with 20mV increment. The reversal potential in this bi-ionic system was detected to be −1.71±0.49 mV. This value, near zero mV, means that the channel which is opened by 12-HPETE is permeable to $Na^+$ as well as $K^+$. For the permeability ratio of $K^+/Na^+$ ($P_K/P_{Na}$), 1.1. was calculated from this bi-ionic system experiment, indicating that the channel opened by 12-HPETE is also permeable to $K^+$ ion, like the channel opened by CAP.

Taken together, the results above obtained demonstrate that 12-HPETE directly activates the channel which is opened by CAP, that is, the CAP-channel.

EXAMPLE II

Agonistic Potency of Various Lipoxygenase Metabolites

In order to compare the agonistic potencies of the various metabolites synthesized by the action of various lipoxygenases, one patch was administered with 0.5 μM of CAP and then, with various lipoxygenase metabolites. At each experiment, the open probabilities (Po) of the channel attributable to the metabolites were recorded and calculated as a percentage to the open probability obtained at 0.5 μM CAP.

Figure 7:
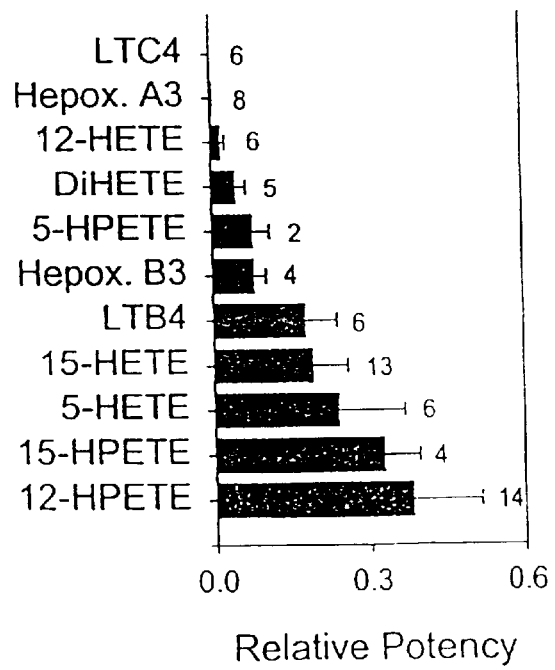
FIG. 7 is a histogram showing the relative potency of LO metabolites administered with 10 $\mu$M of each of the lipoxygenase metabolites at a relative to the channel open probability caused by administration of 0.5 $\mu$M of CAP, where the channel potency is measured by a single channel recording method and represented by NPo wherein N represents how many the channel is opened and Po represents how often the channel is opened. In the graph, HPETE is an abbreviation for hydroperoxyeicosatetraenoic acid, HETE for hydroxyeicosatetraenoic acid, Hepox A3 for hepoxilin A3, Hepox B3 for hepoxilin B3, DiHETE for dihydroxy eicosatetraenoic acid, LTB4 for leukotriene B4, and LTC4 for leukotriene C4.

All of the lipoxygenase metabolites tested were administered at an amount of 10~20 μM to the membrane patches of cultured sensory neurons. The relative potency of the metabolites in activating the channel was depicted in FIG. 7. As apparent from this histogram, almost all of the lipoxygenase metabolites, if different in agonistic potency, activate the CAP channel. Of them, 12-HPETE shows the highest agonistic potency.

Figure 8A:
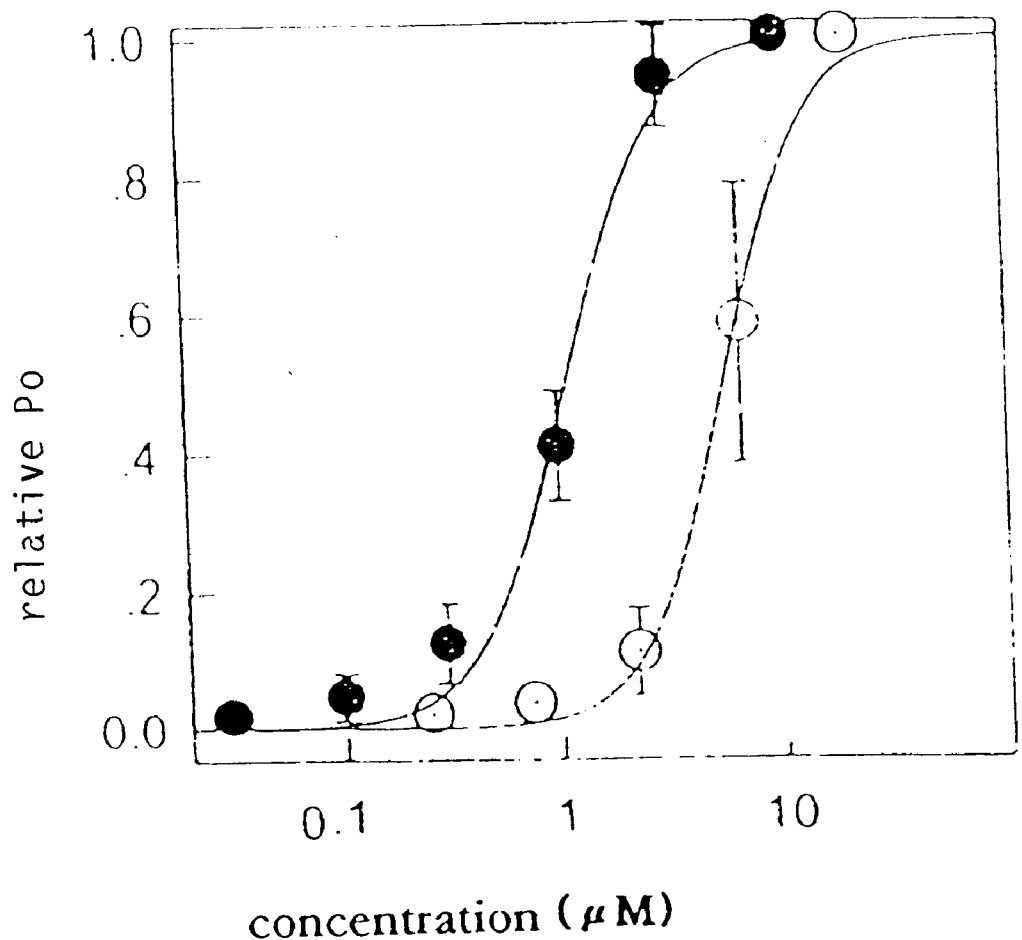
FIG. 8a is a concentration-response curve obtained after 12-HPETE was administered at various concentrations to membrane patches of sensory neurons. In the figure, the symbol ● represents 12-HPETE and the symbol ○ represents CAP.
Figure 8B:
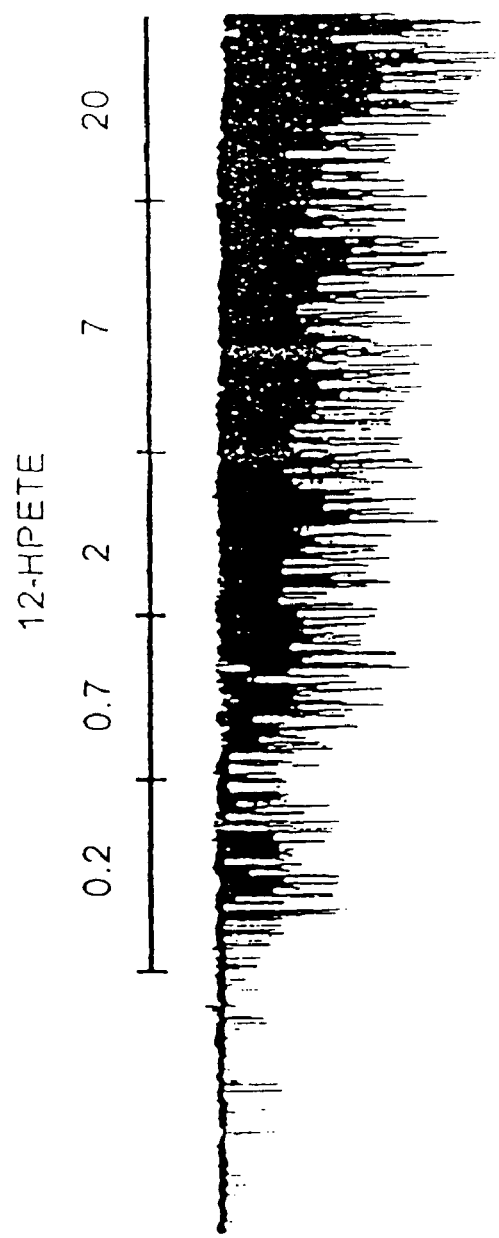
FIG. 8b shows the single-channel currents of CAP channels, which is gradually increased as the amount of 12-HPETE increases from 0.1 $\mu$M to 20 $\mu$M.

12-HPETE was administered at various concentrations from 0.25 to 20 μM to the cell membrane patches of sensory nerve cells, in order to plot a concentration-response curve. As a result, FIG. 8a was obtained. The activation of the channel was observed to be the highest at 20 μM of 12-HPETE as measured by use of a single channel current recording with the aid of a patch clamp technique, as shown in FIG. 8b. Returning now to FIG. 8a, the channel activation currents obtained at each 12-HPETE concentration were calculated as relative degrees to the channel activation current obtained at 20 μM of 12-HEPETE. The relative channel degrees were plotted against the concentrations of 20 μM 12-HPETE and the resulting plot followed the Hill equation. As obtained from this plot, the half-maximal dose ($EC_{50}$) of 12-HPETE in activating the channel was 4.7 μH. In addition, the Hill coefficient of 12-HPETE was determined to be 2.4, just like that of CAP, suggesting that at least two ligands are necessary for the activation of the channel.

EXAMPLE III

Figure 9:
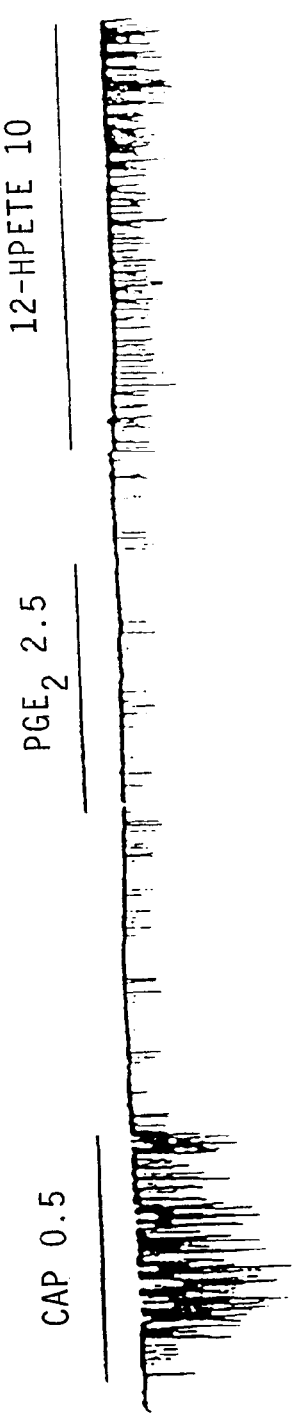
FIG. 9 shows the single-channel currents of CAP channels, obtained by administering prostaglandin E$_2$ (PGE$_2$) to a membrane patch of a sensory neuron.

Activity of Prostaglandins and Arachidonic Acid in Activation of CAP Channel An examination was made on the activity of prostaglandins in activating CAP channels because they are unsaturated fatty acids produced from arachidonic acid by the catalytic action of the enzyme cyclooxygenase. As in 12-HPETE, $PGE_2$, $PGD_2$ and $PGI_2$ were administered 15 times, 4 times and twice, respectively, to the intracellular side of the CAP channel. However, no channel currents were generated by such metabolites of arachidonic acid while 12-HPETE caused channel currents in the same cell membrane patch, as depicted in FIG. 9. These results demonstrate that the CAP channel is activated by the lipoxygenase metabolites, but not by the cyclooxygenase metabolites, although both of them come from arachidonic acid in vivo.

Figure 10:
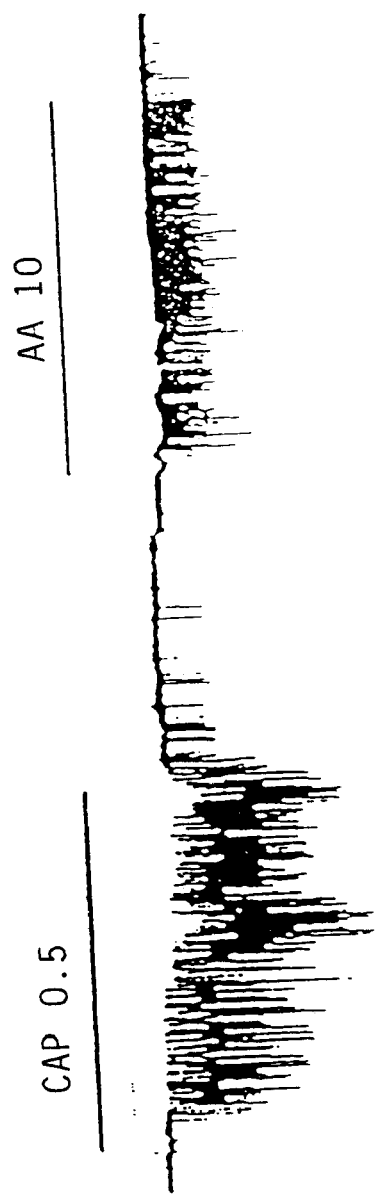
FIG. 10 shows the single-channel currents of CAP channels, obtained by administering arachidonic acid to a membrane patch of a sensory neuron.

Based on the reports which disclose that arachidonic acid, a precursor of 12-HPETE, directly activates other channels and functions as a second messenger in various cells (Wallert et al., 1991; Kim et al., 1995), account was taken of the possibility that arachidonic acid might have an activating influence on the CAP channels, To examine the possibility, arachidonic acid was administered to membrane patches containing CAP channels, When being used at amounts from 10 to 50 μM, arachidonic acid failed in activating the,CAP channels in approximately 46% of the experiments tried (32 of 69 trials). On the other hand, in the remaining 54%, arachidonic acid weakly induced channel currents, as shown in FIG. 10. However, the weak activation of arachidonic acid on the channel was believed to result from the conversion of arachidonic acid into its metabolite, that is, 12-HPETE by the catalytic action of the lipowygenase present in the cell membrane of the patch, rather than from the direct action of arachidonic acid on the Channel.

Figure 11:
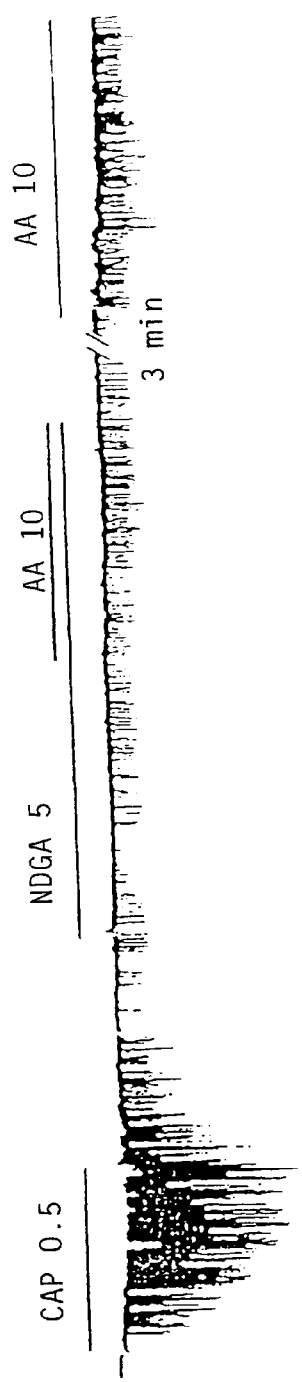
FIG. 11 shows the activity of CAP channels, obtained by administering arachidonic acid, alone and in combination with nordihydroguaiaretic acid (NDGA), to cell membrane patches of sensory netve cells, demonstrating that the single channel current generated by arachidonic acid is reversibly controlled depending on the presence or absence of NDGA.

Thus, in order to know whether the channel activation of arachidonic acid is -due to the catalytic action of lipoxygenase, nordihydrouaiaretic acid (NDGA), known as a non-specific lipoxygenase inhibitor, was administered together with arachidonic acid, The generation of a single channel current by arachidonic acid was reversibly controlled depending on the presence or absence of NDGA, as seen in FIG. 11. Therefore, the channel activation of arachidonic acid was proved to be attributed to the metabolites of arachidonic acid produced by the catalytic action of lipoxygenase.

Consequently, the above results demonstrate that only the lipoxygenase metabolites of arachidonic acid can activate CAP channels with inability in the cyclooxygenase metabolites.

EXAMPLE IV

Analysis for Structure of Lipoxygenase Metabolites

From the data obtained in the above examples, it was recognized that CAP and the lipoxygenase metabolites bind to the same site of the CAP channel. This fact provided a base for analyzing the structural similarity between CAP and the lipoxygenase metabolites although they are quite different in the origin for their synthesis. In this example, an examination was made on the structural correlation between them.

To compare the structures of CAP and 12-HPETE, the structures of CAP and 12-HPETE in their lowest energy state were first obtained using a molecular modeling algorithm, followed by superimposing their three-dimensional images with each other.

Figure 3:
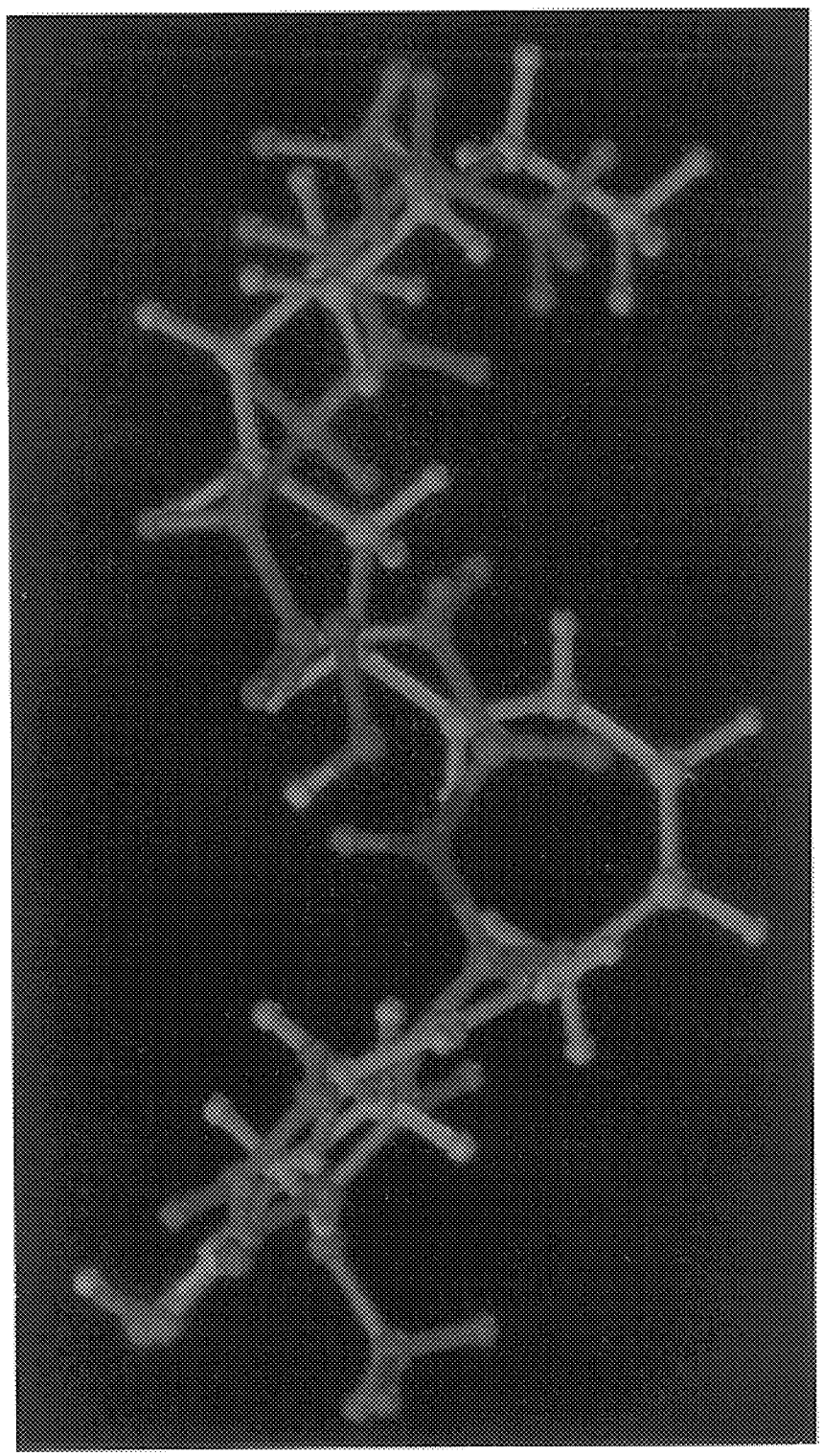
FIG. 3 shows a molecular structure of 12-hydroperoxyeicostetraenoic acid (12-HPETE), which is superimposed on a molecular structure of capsaicin at their lowest energy states.

At its lowest energy statem, i.e., most stable state in an aqueous solution, 12-HPETE was observed to have a lengthy hydrophobic extending moiety and a curved moiety with 12(s)-hydroperoxide group as the central point. This structure of 12-HPETE was superimposed on the structure of CAP. In this regard, the amide group of CAP, the hydroperoxide of 12-HPETE and the hydrocarbon chain of each molecule were brought into comparison foci. The two structures were quite overlapped with each other, as shown in FIG. 3. This structural homology between CAP and 12-HPETE well describes various phenomena appearing in the synthesis of CAP. To have a polar aromatic head and a hydrophobic tail is one of the structural requirements for exhibiting agonistic potency for CAP channels. The lacking of hydroxy group of methoxy group out of the aromiatic ring resulted in a loss of the activation potency. It was also found that the alkyl chain suitable for the activation potency was to contain 8~10 carbon atoms. The lipoxygenase metablites which are poor in the activation potency for CAP channels, such as leukotriene $B_4$, were low in the structural homology with CAP.

Such structural homology between 12-HPETE and CAP account for why CAP acts like 12-HPETE, an dndogenous ligand for CAP channels, in cells, Reversely, their identical or similar action on the channel may suggest that they are identical of similar in structure. Therefore, the data obtained in this experiment indicate that CAP derivatives, if synthesized, have to meet the structural requirement in order to show agonistic or antagonistic effects on CAP channels, Because the endogenous ligand of the CAP channels had not been revealed thus far, there was no well established no structural analysis in order for CAP like substance to act as agonists or antagonists. However, the present invention disclosing the endogenous ligand makes easy structural designs for the agonists and antagonists of CAP channels.

EXAMPLE V

Correlation of Bradykinin With CAP Channel

Although 12-HPETE, a product as a result of the catalytic action of lipoxygenase, was identified as an endogenous ligand for CAP channels, there was still yet not found the entity which makes 12-HPETE synthesized in sensory neurons so as to open CAP channels.

In this example, the biological signal which orders CAP channels to be activated in vivo was examined.

Bradykinin (hereinafter referred to as 'BK') is known as a substance which, when a pathological state, such as inflammation, is synthesized and released in the peripheral Inflamed tissues to cause strong pain (Campbell and Meyer, 1986; Taiwo et al., 1990; Rueff and Dray, 1993). BK is also known to stimulate arangidonic acid synthesis from nerve cells and increases the concentration of $Ca^{2+}$ in cells, giving an impulse to the nerve cells. However, no accurate encitation mechanisms of nerve cells have been recognized so far.

When taking various experimental results previously obtained into account, it was inferred that BK has a possibility to open CAP channels through the arachidonic acid-lipoxygenase pathway. To confirm this inference, an examination was made regarding whether the currents generated in cultured sensory nerve sells in response to BK were diminished by CZP or other lipoxygenase inhibitors. If BK made CAP channel open via the arachidonic acid-lipoxygenase pathway, the current response to BK must be reduced by CZP. However, rarely did the cultured cells respond to BK. Only ten of 164 cultured cells showed inward whole-cell currents in response to 1~5 $\mu$M of BK.

Figure 12:
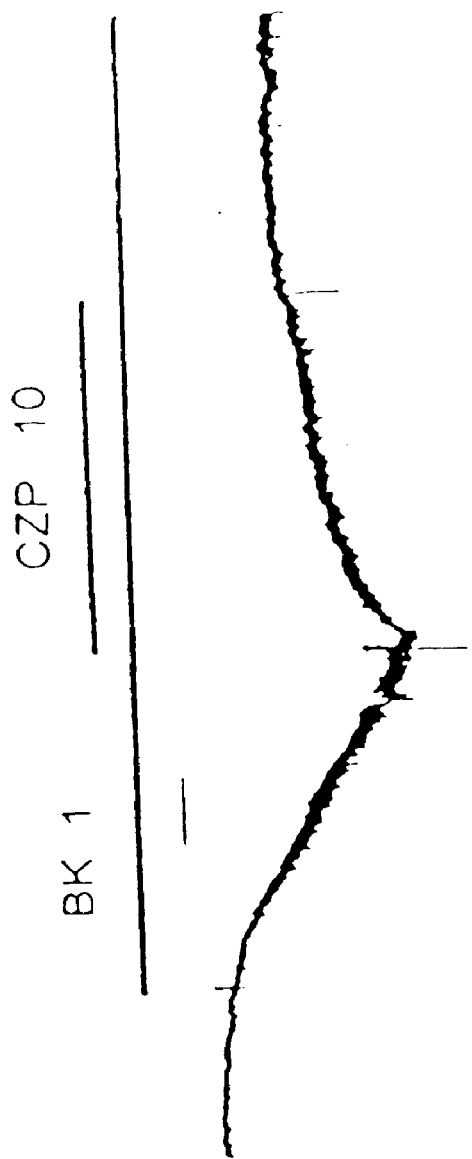
FIG. 12 shows the action of bradykinin which is exerted on CAP channels via the arachidonic acid-lipoxygenase pathway.

BK and CZP were administered to the cells which showed such a response. As seen in FIG. 12, the administration of CZP at a dose of 10 $\mu$M reduced the current generated by 5 $\mu$M of BK, which indicates that BK opens CAP channels via the arachidonic acid-lipoxygenase pathway to generate inward whole-cell currents in certain kinds of sensory neurons.

Figure 13A:
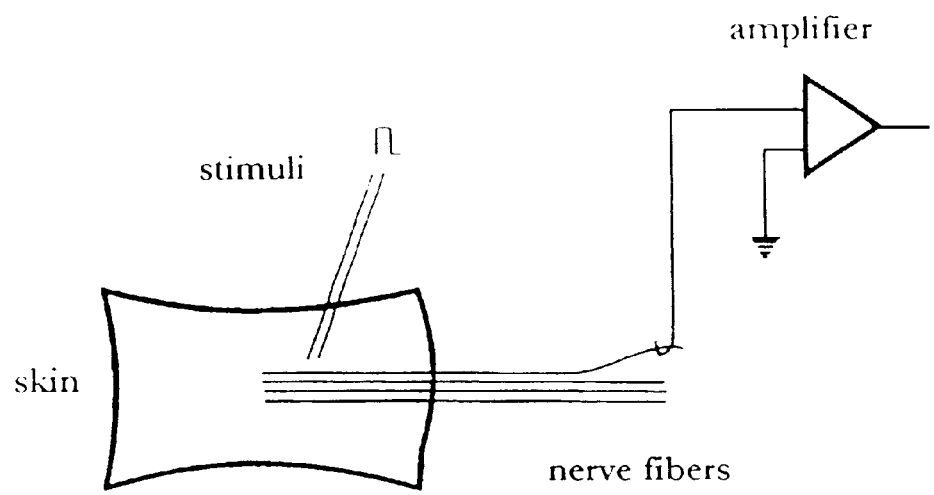
FIG. 13a is a schematic view illustrating a skin-nerve preparation for measuring the action potentials of the pain nerves of the skin.
Figure 13B:
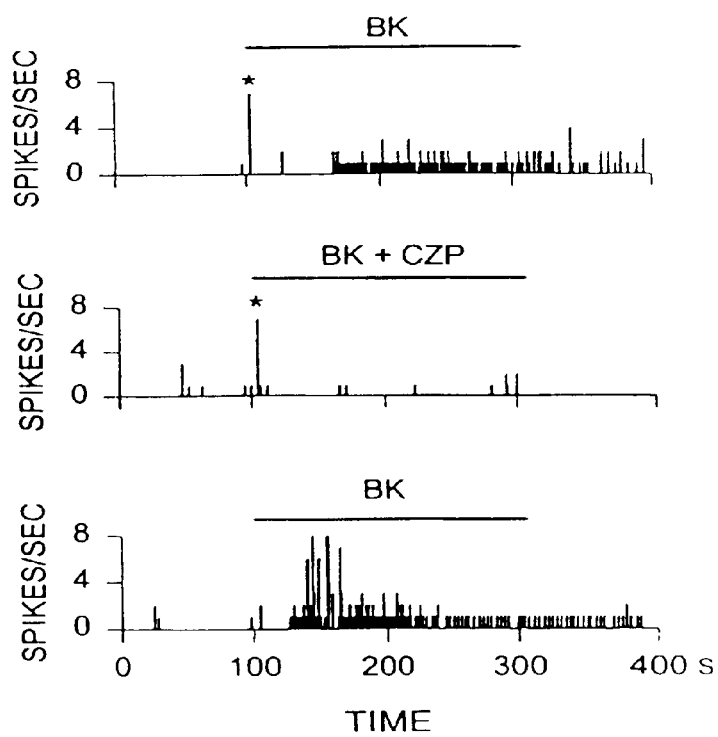
FIG. 13b shows the action potential of the cutaneous nerve in response to CAP, BK and a CAP-receptor antagonist, CZP.

To recognize whether the excitation of BK on nerve cells is accomplished via the arachidonic acid-lipoxygenase-CAP pathway, in vivo, a measurement was made on the action potentials in the sensory nerve fibers of the rats, as shown in FIGS. 13a and 13b. particularly, pain nerves which exist in the skin were isolated, together with a overlapping area of the skin, and the action potentials were measured from the nerve filaments using skin-nerve preparation (Reeh, 1998; Steen et al., 1992, 1995) as schematically illustrated in FIG. 13a. While unit action potentials measured at the sensory nerve fibers isolated from the skin, frequencies of the action potentials induced by the administration of BK were recorded. An increase in frequency of the action potentials means excitation of the sensory nerves.

The transmission speed of nerve signals were measured and only c-fibers (non-myelinated sensory nerve fibers) were used in the BK response experiment. The reason why c-fibers are used only is that they consist mainly of pain nerve cells (Willis and Coggeshall, 1991; Yaksh, 1986).

Figure 13C:
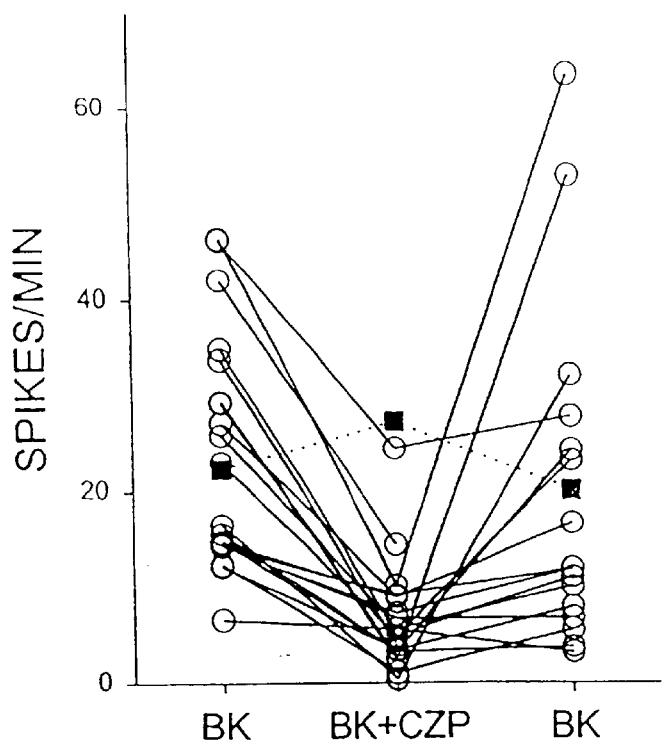
FIG. 13c shows the great suppressive action of CZP on the action potential of the cutaneous nerve which is increased by BK, as recorded from 28 cutaneous nerves.

With reference to FIG. 13b, there are illustrated the action potential behaviors of the cutaneous pain nerve in response to agonist and antagonist samples. As seen in the uppermost graph, CAP administration largely increased action potentials of the nerve fibers. Administration of 1 $\mu$M of BK to this skin patch also made the nerve cells excited although the excitation magnitude was not as large as that obtained upon the addition of CAP. In order to recognize whether the nerve excitation of BK was attributed to the opening of CAP channels, CZP was administered at a dose of 10 $\mu$M, together with BK, to the skin. As seen in FIG. 13, the presence of CZP restrained the current of the BK-activated channels from increasing. An experiment in which BK was administered alone or in combination with CZP to the skin, was repeated 20 times with the aim of testing the influence which BK and a combination of BK and CZP had on the activation of nerve cells, and the results are summarized as shown in FIG. 13c. Great suppression against the response of skin nerve cells to BK was obtained, strongly indicating that the excitation of the sensory nerve fibers requires the activation of CAP channels in the first place.

Figure 14:
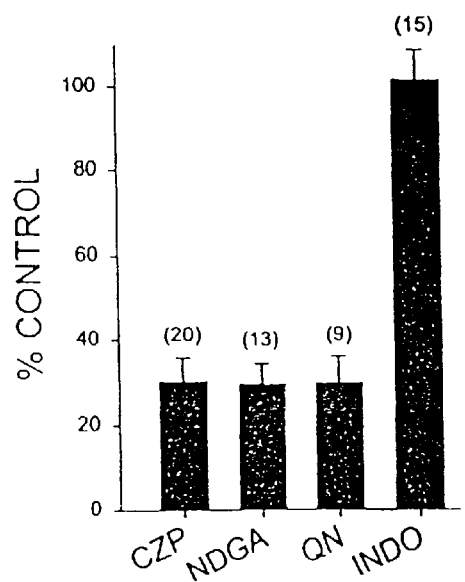
FIG. 14 shows the suppressive action of the inhibitors CZP, NDGA and quinacrin (∴N) on the action potential of the cutaneous neuron which is increased by BK.

When the sensory nerve fibers were excited in response to BK, inhibitors against the enzymes required for the arachidonic acid-lipoxygenase-CAP receptor pathway were used in order to identify whether the response passed through the pathway. The results are given in FIG. 14. In the histogram of FIG. 14, the bar length of each inhibitor represents % activation relative to the activation effect obtained when BK was used alone in absence of any inhibitor. For example, CZP, if added along with BK, suppressed the activation response to BK by approximately %. Quinacrine (QN), which is an inhibitor against phospholipase A2, known to activate arachidonic acid in the cell, showed a suppressive effect by 70% while the activation of BK was lowered by 70% in the presence of 50 $\mu$M of NDGA, a non-specific inhibitor of lipoxygenase. However, the application of 2 $\mu$M indomethacin (INDO), an inhibitor of cyclooxygenase, a metabolic enzyme that Converts arachidonic acid to prostaglandins, failed to inhibit the BK response.

Figure 15:
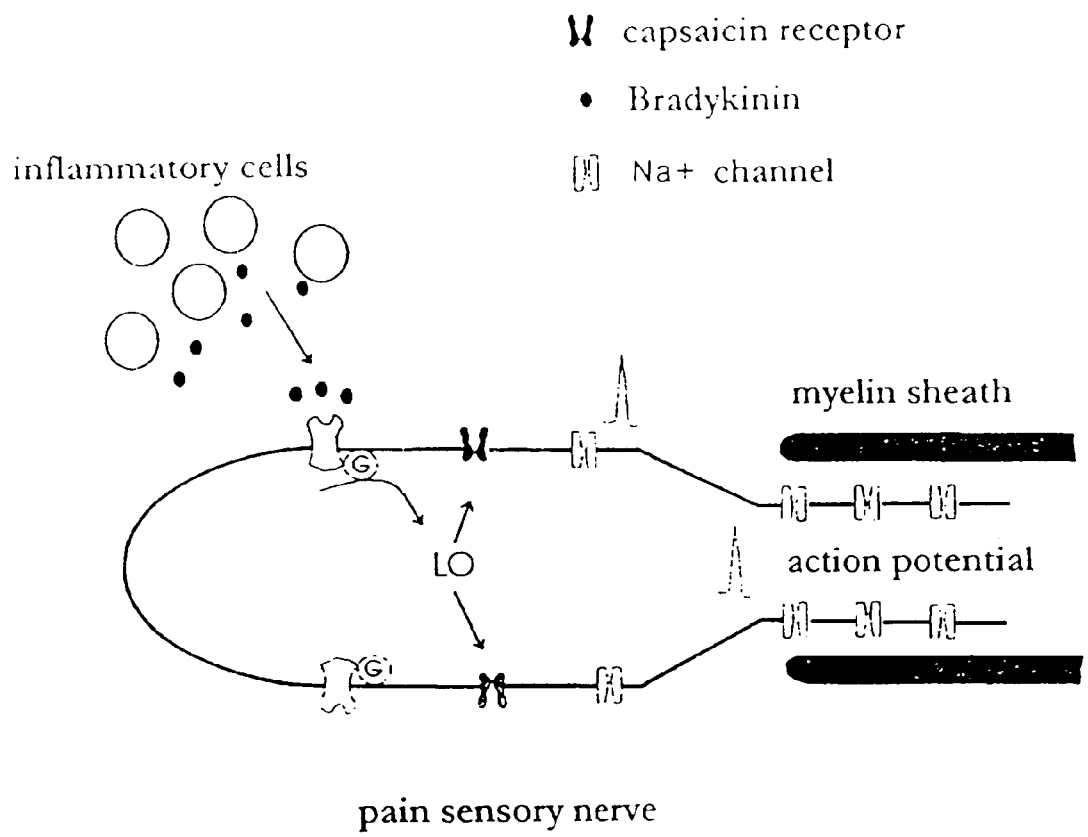
FIG. 15 is a schematic view illustrating the BK-induced ewcitation of a sensory neuron by activating CAP channel revealed first in the world by the present inventors.

From the above results obtained, it was brought to a Conclusion that BK secreted from inflammation cells activates CAP channels via the arachidonic acid-lipoxygenase pathway to excite the sensory nerve. This BK-initiated CAP channel activation mechanism is schematically depicted in FIG. 15.

The present invention has been described in an illustrative manner, and it is to be understood the terminology used is intended to be in the nature of description rather than of limitation. Many modifications And variations of the present invention are possible in light of the above teachings. Therefore, it is to be understood that within the scope of the appended claims, the invention may be practiced otherwise than as specifically described.

What is claimed is:

1. A method for activation of capsaicin channel, which comprises administering to an individual a composition containing as an effective ingredient at least one lipoxygenase metabolite of arachidonic acid acting as an endogeneous ligand for capsaicin-channel or capsaicin-receptor, wherein the at least one lipoxygenase metabolite is 12-hydroperoxyeicosatetraenoic acid.

* * * * *